(12) United States Patent
Technow et al.

(10) Patent No.: US 11,980,147 B2
(45) Date of Patent: May 14, 2024

(54) MOLECULAR BREEDING METHODS

(71) Applicant: PIONEER HI-BRED INTERNATIONAL, INC., Johnston, IA (US)

(72) Inventors: Frank Technow, Waterloo (CA); Liviu Radu Totir, Johnston, IA (US)

(73) Assignee: PIONEER HI-BRED INTERNATIONAL INC., IA (US)

( * ) Notice: Subject to any disclaimer, the term of this patent is extended or adjusted under 35 U.S.C. 154(b) by 0 days.

(21) Appl. No.: 15/536,556

(22) PCT Filed: Dec. 10, 2015

(86) PCT No.: PCT/US2015/064881
§ 371 (c)(1),
(2) Date: Jun. 15, 2017

(87) PCT Pub. No.: WO2016/100061
PCT Pub. Date: Jun. 23, 2016

(65) Prior Publication Data
US 2017/0359978 A1    Dec. 21, 2017

Related U.S. Application Data

(60) Provisional application No. 62/093,713, filed on Dec. 18, 2014.

(51) Int. Cl.
*A01H 1/04* (2006.01)
*G16B 20/00* (2019.01)
*G16B 20/20* (2019.01)
*G16B 20/40* (2019.01)

(52) U.S. Cl.
CPC .............. *A01H 1/04* (2013.01); *G16B 20/00* (2019.02); *G16B 20/20* (2019.02); *G16B 20/40* (2019.02)

(58) Field of Classification Search
CPC ....................................................... A01H 1/04
USPC ........................................................ 800/267
See application file for complete search history.

(56) References Cited

U.S. PATENT DOCUMENTS

| | | |
|---|---|---|
| 2005/0144664 A1 | 6/2005 | Smith et al. |
| 2008/0163824 A1 | 7/2008 | Moser et al. |
| 2008/0216188 A1 | 9/2008 | Ragot et al. |
| 2010/0095394 A1* | 4/2010 | Bink ............ G06F 19/18 800/264 |
| 2011/0098195 A1 | 4/2011 | Russwurm |
| 2014/0123330 A1 | 5/2014 | Carlson et al. |
| 2014/0220568 A1 | 8/2014 | Inze et al. |

FOREIGN PATENT DOCUMENTS

| | | |
|---|---|---|
| WO | 2009108802 A2 | 9/2009 |
| WO | 2014200348 A1 | 12/2014 |
| WO | 2015100236 A1 | 7/2015 |
| WO | 2015155607 A2 | 10/2015 |

OTHER PUBLICATIONS

Schulz-Streeck et al., 2012, Crop Science 52: 2453-2461.*
Rincent et al., 2012, Genetics 192: 715-728.*
Gelman, 2006, Multilevel (Hierarchical) Modeling: What It Can and Cannot Do, Technometrics 48: 432-435.*
Gelman and Pardoe, 2004, Bayesian Measures of Explained Variance and Pooling in Multilevel (Hierarchical) Models, EERI Research Paper Series No. Apr. 2004, pp. 1-21.*
Andrew Gelman, 2006, Prior distributions for variance parameters in hierarchical models (Comment on Article by Browne and Draper), Bayesian Analysis 1: 515-534.*
Brøndum et al., 2012, Genome position specific priors for genomic prediction, BMC Genomics 13:543, pp. 1-11.*
Andrew Gelman and Jennifer Hill, 2006, Data Analysis Using Regression and Multilevel/Hierarchical Models, Cambridge University Press, available at http://www.stat.columbia.edu/~gelman/arm/, pp. 1-648, Table of Contents only.*
Li, 2006, Statistical Models of Sequencing Error and Algorithms of Polymorphism Detection, PhD Thesis, University of Southern California, pp. 1-133.*
Mackay et al., Handbook of Statistical Genomics, 501-530 (Year: 2019).*
Belhaj, K. et al., "Plant genome editing made easy: targeted mutagenesis in model and crop plants using the CRISPR/Cas system", 2013, Plant Methods, vol. 9(1): 39.
Fan, L. et al., "Urinary sodium excretion and kidney failure in nondiabetic chronic kidney disease", 2014, Kidney International, 86, 582-288.
Goldstein, L.J. et al., "A computer model of the kidney", 1992, Computer Methods and Programs in Biomedicine, 37, 191-203.
Thiele, I. et al., "A community-driven global reconstruction of human metabolism", 2013, Nature Biotechnology, vol. 31(5): 419-425.
Uttamsingh, R.J. et al., "Mathematical model of the human renal system", 1985, Medical & Biological Engineering & Computing, 525-535.
Zhao, Y. et al., "Impact of selective genotyping in the training population on accuracy and bias of genomic selection", 2012, Theoretical and Applied Genetics, vol. 125(4): 707-713.
International Search Report and Written Opinion of the International Searching Authority for Application PCT/US15/43525, dated Dec. 30, 2015.

(Continued)

*Primary Examiner* — Li Zheng

(57) ABSTRACT

A Bayesian multilevel whole-genome regression model is disclosed and its prediction performance compared to that of the popular BayesA model applied to each population separately (no pooling) and to the joined data set (complete pooling). For small population sizes (e.g., <50), partial pooling increased prediction accuracy over no or complete pooling for populations represented in the estimation set. Partial pooling with multilevel models can make optimal use of information in multi-population estimation sets.

7 Claims, 2 Drawing Sheets

(56) References Cited

OTHER PUBLICATIONS

International Search Report and Written Opinion of the International Searching Authority for Application PCT/US15/64881, dated Feb. 12, 2016.
Zhong, Shengqiang, et al., "Using Quantitative Trait Loci Results to Discriminate Among Crosses on the Basis of Their Progeny Mean and Variance," 2007; Genetics, 177:567-576.
Technow, Frank, et al., "Using Bayesian Multilevel Whole Genome Regression Models for Partial Pooling of Training Sets in Genomic Prediction", Aug. 2015, G3, vol. 5, pp. 1603-1612.
Heng-De L., et al., "Genome Selection and its Application," Heritage [Y] 1-9, 2011, vol. 11, No. 13, pp. 1308-1316. English language copy from machine translation.
International Preliminary Report on Patentability for International Application No. PCT/US2015/064881, mailed Jun. 29, 2017, 8 Pages.
Jannink J.L., et al., "Genomic Selection in Plant Breeding: from Theory to Practice," Briefings in Functional Genomics, Feb. 15, 2010, vol. 9, No. 2, pp. 166-177.
Zhenming Z., et al., "Multilevel Bayesian Model Prediction of Forest Soil Total Nitrogen," Acta Ecologica Sinica, 2009, vol. 29 (10), pp. 5675-5683. English language copy from machine translation.
R. Rincent et al., Maximizing the Reliability of Genomic Selection by Optimizing the Calibration Set of Reference Individuals: Comparison of Methods in Two Diverse Groups of Maize Inbreds (*Zea mays* L.), pp. 715-728 and Support Information pp. 1-4, Oct. 2012, Genetics, vol. 192.†
Christina Lehermeier et al., Usefulness of Multiparental Populations of Maize (*Zea mays* L.) for Genome-Based Prediction, pp. 3-16, Sep. 2014, Genetics, vol. 198.†
Zhou et al., Genomic Predictions Across Nordic Holstein and Nordic Red Using the Genomic Best Linear Unbiased Prediction Model with Different Genomic Relationship Matrices, pp. 249-257, 2014, Journal of Animal Breeding and Genetics vol. 131, Blackwell Verlag Gmbh.†
M. Erbe et al., Improving Accuracy of Genomic Predictions within and between Dairy Cattle Breeds with Imputed High-Density Single Nucleotide Polymorphism Panels, pp. 4114-4129, 2012, Journal of Dairy Science vol. 95.†
T. Schulz-Streek et al., Genomic Selection Using Multiple Populations, pp. 2453-2461, Nov.-Dec. 2012, Madison, WI.†

* cited by examiner
† cited by third party

MOLECULAR BREEDING METHODS

CROSS-REFERENCE TO RELATED APPLICATIONS

This application is a 371 national stage entry of PCT patent application PCT/US15/064881, filed Dec. 10, 2015, which claims priority to U.S. Provisional Application No. 62/093,713 filed Dec. 18, 2014, each of which is hereby incorporated by reference in its entirety.

BACKGROUND

Estimation set size is an important determinant of genomic prediction accuracy. Plant breeding programs are characterized by a high degree of structuring, particularly into populations. This hampers establishment of large estimation sets for each population.

The use of genomic selection in animal and plant breeding is based on the ability to generate accurate genomic estimated breeding values (GEBV). An important determinant of prediction accuracy is the size of the estimation set. In animal breeding, assembling large single-breed estimation sets is relatively straight forward for dairy breeds like Holstein Friesian, where genomic selection is applied most successfully to date. However, for some dairy cattle breeds and in particular for beef cattle breeds, assembling single-breed estimation sets of sufficient size is often not possible. Creation of multi-breed estimation sets by pooling data from several breeds together, is therefore of great interest and subject of active research.

A similar situation exists in plant breeding, which is characterized by a high degree of breeder induced structure. This structure results from the importance of keeping distinct heterotic groups for maximum exploitation of heterosis, from use of distinct biparental breeding populations and the need for specialized breeding programs targeting specific traits or environments. This requires that the phenotyping and genotyping resources available to a breeding program have to be allocated to multiple populations, which can prevent the creation of large estimation sets for each population. Several studies therefore investigated the merit of pooled estimation sets combining populations or even heterotic groups.

However, pooling estimation sets is complicated by differences in genetic properties among populations, such as pertaining to linkage disequilibrium, allele frequencies or relationship structure. This might be the reason that using pooled estimation sets failed to increase prediction accuracy in some applications in plant and animal breeding.

DETAILED DESCRIPTION

It has been proposed to use separate estimation sets for each population but to derive genome position specific priors using data from other populations. In this way, unique genome properties of each population could be accounted for while still using information from other populations. A similar, more formal approach is partial pooling, facilitated by Bayesian multilevel models. In multilevel models, specific marker effects are estimated for each population. However, the prior means of these specific marker effects, which might be interpreted as overall or unspecific marker effects, are estimated from data of all populations, simultaneously with the unspecific marker effects. Because the specific marker effects are shrunk towards the overall effects, the former are still informed by data from the other populations to a certain degree. Partial pooling thus strikes a middle ground between no pooling (specific marker effects estimated from data of the specific population only) and complete pooling (common marker effects estimated from pooled estimation sets).

Pooling populations increases estimation set size but ignores unique genetic characteristics of each. A possible solution is partial pooling with multilevel models, which allows estimating population specific marker effects while still leveraging information across populations.

The objectives were to (i) demonstrate the use of Bayesian multilevel whole-genome regression models for genomic prediction and (ii) investigate scenarios in which partial pooling might be superior over no or complete pooling of estimation sets. These investigations were based on two publicly available maize breeding data sets and supported by a simulation study.

Materials and Methods

Multilevel Whole Genome Regression Model

The statistical model fitted to the data is $$y_{ij} \sim N(\mu_{ij}, \sigma_e^2)$$

$$\mu_{ij} = \beta_0 + \Sigma_k z_{ijk} u_{jk} \qquad 1)$$

where $y_{ij}$ is the observed phenotypic value of the $i^{th}$ individual from the $j^{th}$ population and $\mu_{ij}$ its linear predictor. The phenotypic data $y_{ij}$ was centered to mean zero and scaled to unit variance. The Normal density function, which is used as data model, is denoted as N with $\sigma_e^2$ denoting the residual variance. The common intercept was $\beta_0$. Finally, $u_{jk}$ denotes the additive effect of the $k^{th}$ biallelic single nucleotide polymorphism (SNP) marker in population j. The genotype of individual i from population j at marker k was represented by $z_{ijk}$ and it denotes the number of reference alleles, centered by twice the reference allele frequency. Which of the alleles was chosen as reference allele depended on the data set and is described below. Effects $u_{jk}$ were only estimated when the corresponding marker k was polymorphic in population j. Otherwise it was set to 0 and treated as a constant.

Figure 1A:
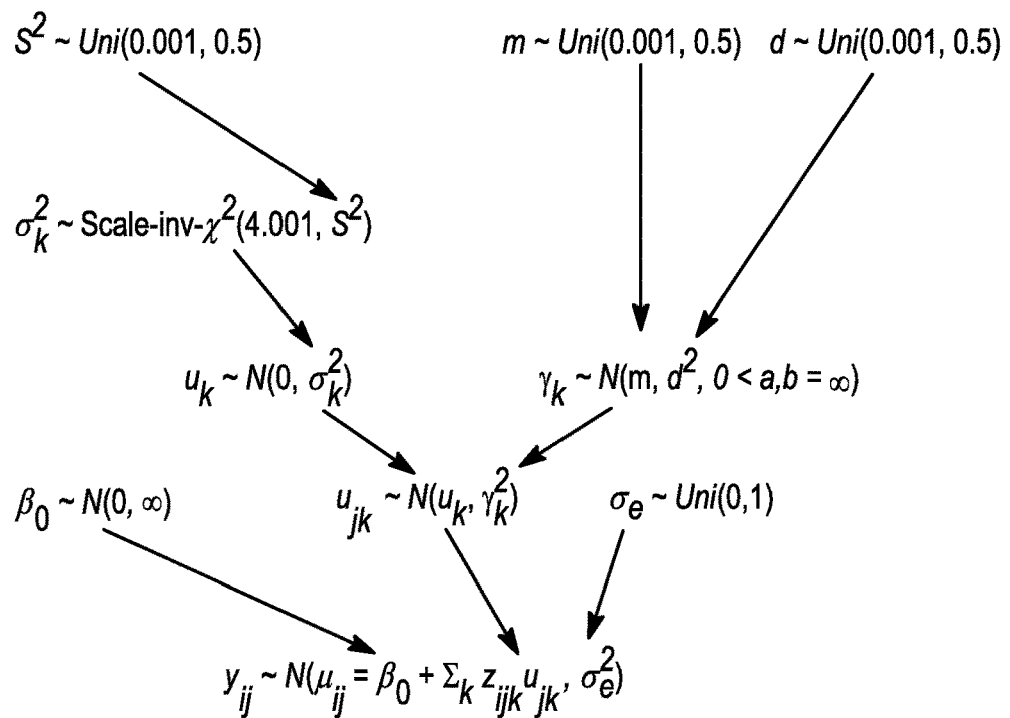
FIG. 1 is a graphical visualization of the multilevel model (A) and the conventional BayesA model (B).

A graphical display of the hierarchical prior distribution setup is shown in FIG. 1A. The prior of $u_{jk}$ is $$u_{jk} \sim N(u_k, \gamma_k^2) \qquad 2)$$

where $u_k$ is the overall effect of the $k^{th}$ marker and the variance parameter $\gamma_k^2$ quantifies the deviations of the specific effects $u_{jk}$ from $u_k$. The shrinkage toward $u_k$ is the stronger the smaller $\gamma_k^2$. Both parameters, $u_k$ and $\gamma_k^2$ are associated with prior distributions themselves and estimated from the data. For $u_k$ this is $u_k \sim N(0, \sigma_k^2)$. Here, the variance parameter $\sigma_k^2$ controls the amount of shrinkage towards 0. It is associated with a scaled inverse Chi-square prior with 4.001 degree of freedom and scale parameter $S^2$. The prior for $u_k$ thus corresponds to the "BayesA" prior.

For the variance parameter $\gamma_k^2$, $$\gamma_k \sim N(m, d^2, 0 < a, b = \infty) \quad (3)$$

which is a Normal distribution prior on $\gamma_k$ with mean parameter m and standard deviation d, left truncated at zero. The mean of the truncated distribution $N(m, d^2, 0 < a b = \infty)$, which is a function of m, d and the truncation points a and b, can be interpreted as the "typical" deviation of the specific marker effects $u_{jk}$ from $u_k$. Higher values of the mean of $N(m, d^2, 0 < a, b = \infty)$ indicate larger deviations and vice versa. This parameter might therefore be used to quantify population divergence.

An uniform prior Uni(0.001, 0.5) is used for the hyperparameters $S^2$, m and d. The prior for the intercept $\beta_0$ is a Normal distribution with mean 0 and a very large variance. For the residual variance $\sigma_e^2$, a uniform distribution prior over the interval [0, 1] on $\sigma_e$ was specified, which agrees with recommendations for uninformative priors on variance components.

Samples from the posterior distribution were drawn with Gibbs sampling, implemented in the JAGS Gibbs sampling environment. The total number of samples used for inference was 1000, drawn from a single chain of length 510000. The first 10000 samples were discarded as burn in and only every 500th subsequent sample stored. These settings ensured convergence and an effective sample size (ESS) of >100 for all parameters (ESS of $u_k$ and $u_{jk}$ were typically >500).

The ESS was calculated with the R package CODA, which was also used to monitor convergence using diagnostic plots.

Conventional Whole Genome Regression Model

Figure 1B:
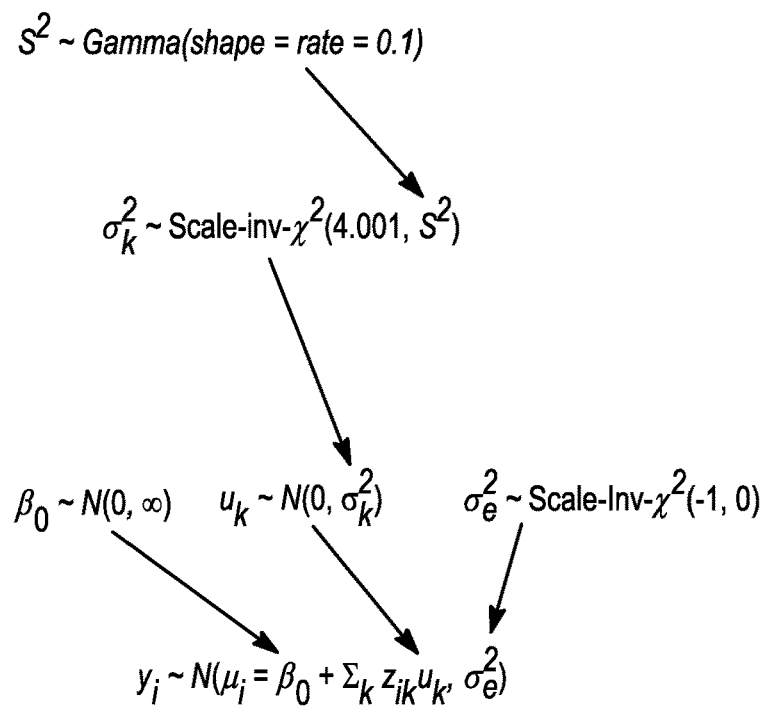

The Bayesian whole genome regression method "BayesA" was used, with modifications pertaining to the hyperparameter $S^2$ (see FIG. 1B for a graphical representation). The linear model is $$y_{ij} \sim N(\mu_{ij}, \sigma_e^2)$$

$$\mu_{ij} = \beta_0 + \Sigma_k z_{ijk} u_k \quad (4)$$

which is the same as model (1), except that the population index j is dropped from the marker effects $u_k$. For no pooling, the model was applied to each population in turn, for complete pooling to the joint data set. For $\sigma_e^2$ an improper scaled inverse Chi-square prior with −1 degrees of freedom and scale equal to zero was used. This is equivalent to a uniform prior on $\sigma_e$, as is used for the multilevel model, but exploits conjugancy.

The BayesA Gibbs Sampler was implemented as a C routine compatible with the R statistical software environment. Again, the total number of samples used for inference was 1000, drawn from a single chain of length 510000, with burn in of 10000 and thinning intervals of 500.

Estimation, Prediction and Testing Procedure

Figure 2:
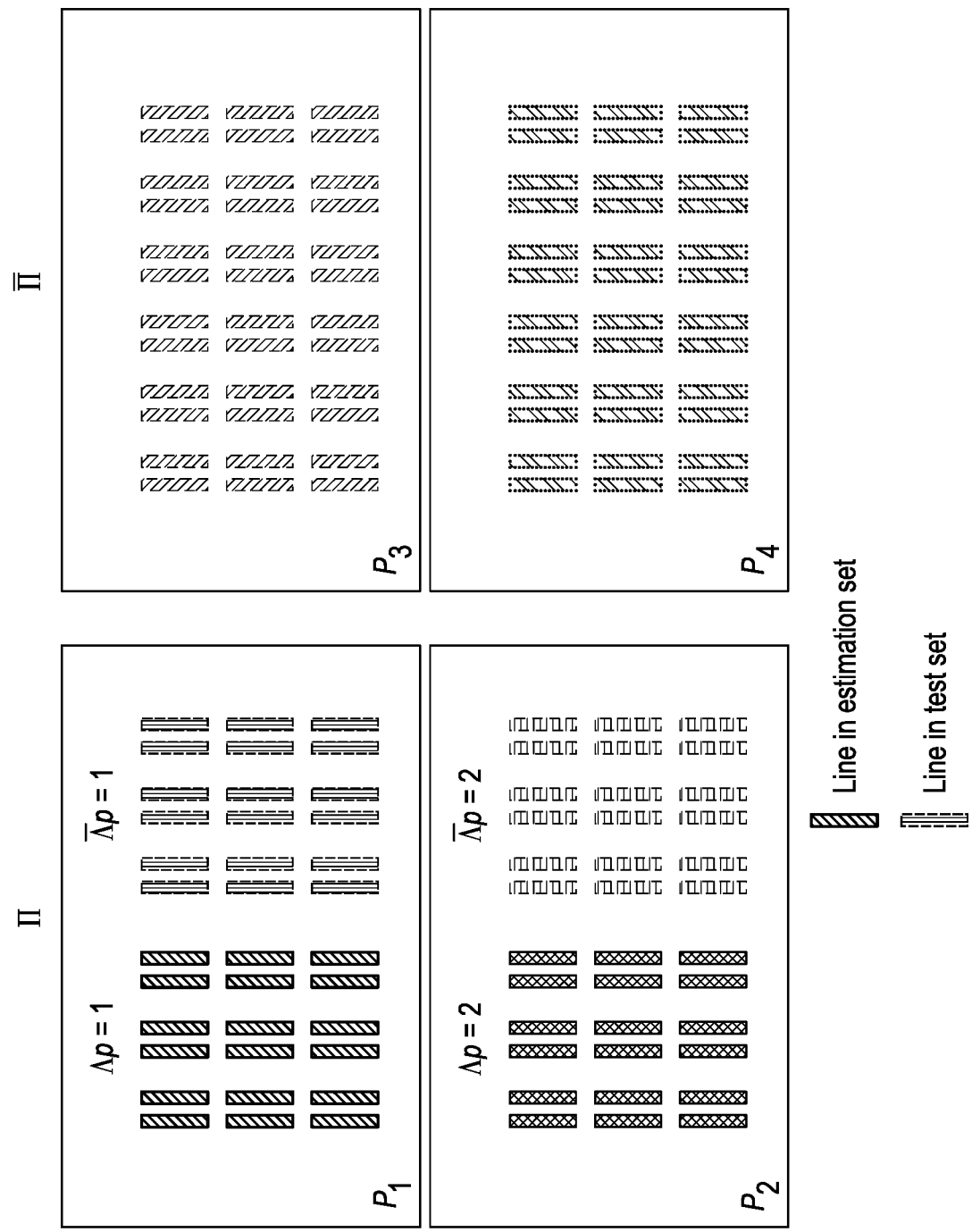
FIG. 2 is a graphical visualization of the testing strategy for evaluating prediction accuracy. The estimation set comprises $\Lambda_1$ and $\Lambda_2$ from populations $P_1$ and $P_2$ (set $\Pi$). The prediction accuracy of lines from populations represented in estimation set ($r_\Pi$) was computed from $\Lambda_1$ and $\Lambda_2$, the prediction accuracy of lines from populations not represented in estimation set from lines in $P_3$ and $P_4$ (set $\overline{\Pi}$).

Let Π denote the set of P populations represented in the estimation set and the set of $N_p$ individuals from a population in Π as $\Lambda_p$, where p indexes the populations in Π. A graphical representation is presented in FIG. 2. Further, let those individuals from a population in Π that are not in $\Lambda_p$ be denoted as $\overline{\Lambda}_p$ and the set of populations not in Π as $\overline{\Pi}$. Populations in $\overline{\Pi}$ will be referred to as "new" populations. The estimation set thus comprised all individuals belonging to $\Lambda_p$, for p∈Π. The test set used for calculating prediction accuracy, comprised individuals in $\overline{\Lambda}_p$ from populations in Π and all individuals from populations in $\overline{\Pi}$. The phenotypic observations of test individuals were masked in the estimation procedure. The separation of populations into Π and $\overline{\Pi}$ and of individuals within a population into $\Lambda_p$ and $\overline{\Lambda}_p$ was done at random.

Within each population, prediction accuracy was computed as the correlation between GEBVs and observed phenotypic values of individuals in the testing set. The within population prediction accuracies were subsequently averaged for populations in Π and $\overline{\Pi}$. These average within population prediction accuracies will henceforth be denoted as $r_\Pi$ and $r_{\overline{\Pi}}$. Thus, $r_\Pi$ and $r_{\overline{\Pi}}$ correspond to the prediction accuracy for populations represented and not represented in the estimation set, respectively.

When using partial pooling, GEBVs of individuals in $\Lambda_p$ were predicted using the posterior means of the marker effects estimated for the corresponding population (i.e., $u_{jk}$). GEBVs of individuals from populations in $\overline{\Pi}$ were predicted using the posterior means of the overall (unspecific) marker effects $u_k$.

When using complete pooling, GEBVs of all individuals in the test set were predicted from the posterior means of marker effects $u_k$ estimated from the joint data set with model (4).

Finally, when using no pooling, GEBVs of individuals in $\Lambda_p$ were predicted using the posterior means of the marker effects $u_k$ obtained after applying model (4) to the estimation data from the corresponding set $\Lambda_p$. The no pooling approach does not provide a direct way of predicting GEBVs of individuals from populations in $\overline{\Pi}$. Thus, $r_{\overline{\Pi}}$ was not evaluated for the no pooling approach.

Application to Nested Association Mapping (NAM) Maize Populations

The NAM data set was obtained from the world wide web at panzea.org. It comprised 4699 recombinant inbred lines (RILs) from 25 biparental crosses between a genetically diverse set of maize inbred lines and line B73 as common parent. The average population size was 188. The RILs were genotyped with 1106 polymorphic SNP markers covering the whole genome. The non-B73 allele was defined as the reference allele. All SNP were biallelic and thereby the reference allele corresponded to the same nucleotide in all 25 populations. To facilitate computations, a thinned set of 285 markers was used, chosen in such a way that there was one marker per 5 cM interval, on average. A density of one marker per 10 cM interval is sufficient for genomic prediction in the NAM population. The traits days to silking (DS), ear height (EH), ear length (EL), southern leaf blight resistance (SLB), near-infrared starch measurements (NS) and upper leaf angle (ULA) were analyzed and phenotyped in multi-environment field trials. The phenotypic records used for fitting the models were averages over the single environment phenotypes. The number of environments were 10, 11, 8, 3, 7 and 9 for DS, EH, EL, SLB, NS and ULA, respectively. The traits chosen represent the major trait categories available: yield component (EL), agronomic (EH), disease resistance (SLB), flowering (DS), quality (NS) and morphology (ULA).

To investigate the effect of total number of lines N, number of populations P and number of lines per population $N_p$ in the estimation set on prediction accuracy and the relative performance of the pooling approaches, the following combinations of P and $N_p$ were considered: P=5 and $N_p$=50 and 100, P=10 and $N_p$=25, 50 and 100, P=20 and $N_p$=12.5, 25, and 50. For P=20 and $N_p$=12.5, we sampled 19 populations with 12 individuals and one with 22, which results in an average $N_p$ of 12.5. The P and $N_p$ combinations thus gave rise to N of either 250, 500 or 1000. For each combination of trait, P and $N_p$, 50 estimation-testing data sets were generated by repeating the sampling of Π and Λ$_p$ as described above. Throughout, the three pooling approaches were applied to the same data sets. The sampling variation between different data sets thus does not enter the comparisons among pooling approaches.

Application to Interconnected Biparental (IB) Maize Populations

This data set was obtained from the supplement of Riedelsheimer et al. (2013). It comprised 635 doubled haploid (DH) lines from five biparental populations with average size of 127. The populations were derived from crosses between four European flint inbred lines. For all DH lines 16741 SNP markers polymorphic across populations were available. Missing marker genotypes were replaced with twice the frequency of the reference allele, which was the allele with the lower frequency. When analyzing the data we used a thinned set of 285 markers. Because the data set did not include a map of the markers, the markers were chosen randomly.

The DH lines were phenotyped in multi-environment field trials for Giberella ear rot severity (GER), a fungal disease caused by *Fusarium graminearum*, deoxynivalenol content (DON, a major mycotoxin produced by the fungus), ear length (EL), kernel rows (KR) and kernels per row (KpR). A more detailed description of this data set can be found in Riedelsheimer et al. (2013) and Martin et al. (2012).

As described above, populations were randomly split into Λ$_p$ and $\overline{\Lambda}_p$. However, because there were only five populations in total, no populations from Π were excluded. Set $\overline{\Pi}$ was thus empty and $r_{\overline{\Pi}}$ was not evaluated.

The sets Λ$_p$ comprised 25%, 50% and 75% of the lines in each population, which corresponded to an average N$_p$ of 31, 63 and 95, respectively. For each trait and percentage value of estimation individuals, 100 estimation-testing data sets generated, each time resampling the subset of 285 markers too.

Application to Simulated Data Set

A simulation study was conducted to specifically investigate the performance of the pooling approaches under increasing levels of differences in QTL effects among populations. The bases for the simulation were the marker genotypes of the lines in the NAM populations. To simulate genetic values, 20 marker loci were randomly chosen as QTL, which were subsequently removed from the set of observed markers. Additive overall effects a$_q$ were drawn from a standard normal distribution. Then population specific QTL effects a$_{jq}$ were sampled from $N(a_q, \tau_q^2)$. The variance parameter $\tau^2$ was chosen such that the relative standard deviation (rSD), i.e., $\tau_q/a_q$, was equal to 2, 1, 0.5, 0.25 and 0.0. The greater rSD, the less similar the population specific QTL effects are. True genetic values were obtained by summing QTL effects a$_{jq}$ according to the QTL genotypes of each individual. Finally phenotypic values were simulated by adding a normally distributed noise variable to the true genetic values. The variance of the noise variable was chosen such that the heritability across populations was equal to 0.70. The average within family heritability necessarily increased with decreasing rSD, and was 0.53, 0.58, 0.64, 0.68 and 0.70 at rSD 2, 1, 0.5, 0.25 and 0.0, respectively.

Set Π comprised P=10 populations and sets Λ$_p$ had size N$_p$=25. For each rSD value 50 estimation-testing data sets were generated. The QTL positions and effects were randomly generated anew for each data set. Also in this case a thinned set of 285 markers was used. Because the true genetic values were known, $r_\Pi$ and $r_{\overline{\Pi}}$ were computed as the correlation between true genetic values and GEBVs.

Results

NAM Maize Populations

Trends typically held across traits. The results presented and discussed therefore apply to all traits, unless otherwise mentioned.

Increasing N$_p$ while keeping N constant (i.e., having fewer but larger populations in the estimation set) generally increased, $r_\Pi$ and decreased, $r_{\overline{\Pi}}$ (Table 1). However, the increase in $r_\Pi$ was much more pronounced than the decrease in $r_{\overline{\Pi}}$.

When increasing N$_p$ with constant P or when increasing P with constant N$_p$, both $r_\Pi$ and $r_{\overline{\Pi}}$ increased (Table 1). However, while in the first case, $r_\Pi$ and $r_{\overline{\Pi}}$ increased in similar magnitudes, the increase in $r_\Pi$ was much smaller than the increase in $r_{\overline{\Pi}}$ in the second case, in particular when N$_p$ was high. Per definition, the accuracy of no pooling is not expected to change as long as N$_p$ remains constant.

For low P and high N$_p$, e.g., P=5 and N$_p$=100, no pooling achieved the highest $r_\Pi$ and complete pooling the lowest (Table 1). For high P and low N$_p$, e.g., P=20 and N$_p$=25, partial pooling achieved the highest $r_\Pi$. Here no pooling resulted in the lowest $r_\Pi$. The only exception to this was trait DS, where no pooling had a $r_\Pi$ equal or higher to partial and complete pooling also for low N$_p$.

Partial and complete pooling achieved virtually identical prediction accuracies $r_{\overline{\Pi}}$ for new populations (Table 1). In general, $r_{\overline{\Pi}}$ of a particular pooling approach was considerably lower than the corresponding $r_\Pi$. The differences between $r_\Pi$ and $r_{\overline{\Pi}}$ tended to be larger for high N$_p$.

TABLE 1

Average within population prediction accuracies in NAM maize populations. Values shown are average within population prediction accuracies for test individuals, averaged over 50 random estimation-test data splits. The standard errors were <0.013. P gives the size of set Π, i.e., the number of populations represented in the estimation set, column Np gives the number of individuals from each population in Π that were used for estimation, i.e., the sizes of sets Λp. The traits were: days to silking (DS), ear height (EH), ear length (EL), southern leaf blight resistance (SLB), near-infrared starch measurements (NS) and upper leaf angle (ULA).

| P | N$_p$ | trait | no | $r_\Pi$ partial | complete | $r_{\overline{\Pi}}$ partial | complete |
|---|---|---|---|---|---|---|---|
| 5 | 50 | DS | 0.41 | 0.34 | 0.26 | 0.19 | 0.19 |
|   |    | EH | 0.47 | 0.44 | 0.39 | 0.31 | 0.32 |
|   |    | EL | 0.39 | 0.37 | 0.28 | 0.19 | 0.19 |
|   |    | NS | 0.39 | 0.37 | 0.32 | 0.25 | 0.26 |
|   |    | SLB| 0.49 | 0.49 | 0.45 | 0.37 | 0.37 |
|   |    | ULA| 0.50 | 0.48 | 0.44 | 0.36 | 0.36 |

TABLE 1-continued

Average within population prediction accuracies in NAM maize populations. Values shown are average within population prediction accuracies for test individuals, averaged over 50 random estimation-test data splits. The standard errors were <0.013. P gives the size of set Π, i.e., the number of populations represented in the estimation set, column Np gives the number of individuals from each population in Π that were used for estimation, i.e., the sizes of sets Λp. The traits were: days to silking (DS), ear height (EH), ear length (EL), southern leaf blight resistance (SLB), near-infrared starch measurements (NS) and upper leaf angle (ULA).

| P | $N_p$ | trait | no | $r_\Pi$ partial | complete | $r_\pi$ partial | complete |
|---|---|---|---|---|---|---|---|
|  | 100 | DS | 0.52 | 0.41 | 0.28 | 0.21 | 0.20 |
|  |  | EH | 0.57 | 0.51 | 0.43 | 0.34 | 0.34 |
|  |  | EL | 0.49 | 0.46 | 0.35 | 0.23 | 0.23 |
|  |  | NS | 0.47 | 0.44 | 0.36 | 0.29 | 0.29 |
|  |  | SLB | 0.58 | 0.58 | 0.50 | 0.41 | 0.41 |
|  |  | ULA | 0.58 | 0.54 | 0.47 | 0.40 | 0.40 |
| 10 | 25 | DS | 0.32 | 0.28 | 0.22 | 0.18 | 0.17 |
|  |  | EH | 0.38 | 0.38 | 0.35 | 0.30 | 0.31 |
|  |  | EL | 0.31 | 0.31 | 0.25 | 0.21 | 0.21 |
|  |  | NS | 0.30 | 0.33 | 0.30 | 0.26 | 0.27 |
|  |  | SLB | 0.40 | 0.46 | 0.43 | 0.38 | 0.39 |
|  |  | ULA | 0.39 | 0.44 | 0.41 | 0.36 | 0.37 |
|  | 50 | DS | 0.42 | 0.35 | 0.26 | 0.22 | 0.22 |
|  |  | EH | 0.47 | 0.45 | 0.40 | 0.36 | 0.36 |
|  |  | EL | 0.40 | 0.39 | 0.29 | 0.23 | 0.23 |
|  |  | NS | 0.38 | 0.40 | 0.35 | 0.30 | 0.30 |
|  |  | SLB | 0.49 | 0.52 | 0.46 | 0.42 | 0.43 |
|  |  | ULA | 0.48 | 0.50 | 0.45 | 0.41 | 0.41 |
|  | 100 | DS | 0.51 | 0.42 | 0.30 | 0.25 | 0.25 |
|  |  | EH | 0.57 | 0.53 | 0.44 | 0.39 | 0.39 |
|  |  | EL | 0.48 | 0.46 | 0.33 | 0.27 | 0.27 |
|  |  | NS | 0.48 | 0.46 | 0.38 | 0.33 | 0.33 |
|  |  | SLB | 0.57 | 0.57 | 0.49 | 0.45 | 0.45 |
|  |  | ULA | 0.59 | 0.57 | 0.48 | 0.44 | 0.44 |
| 20 | 12.5 | DS | 0.23 | 0.23 | 0.21 | 0.17 | 0.17 |
|  |  | EH | 0.28 | 0.34 | 0.33 | 0.30 | 0.31 |
|  |  | EL | 0.22 | 0.27 | 0.23 | 0.19 | 0.19 |
|  |  | NS | 0.21 | 0.30 | 0.29 | 0.27 | 0.28 |
|  |  | SLB | 0.31 | 0.43 | 0.42 | 0.38 | 0.39 |
|  |  | ULA | 0.28 | 0.40 | 0.39 | 0.35 | 0.36 |
|  | 25 | DS | 0.32 | 0.30 | 0.24 | 0.22 | 0.23 |
|  |  | EH | 0.38 | 0.42 | 0.39 | 0.36 | 0.37 |
|  |  | EL | 0.31 | 0.34 | 0.28 | 0.22 | 0.22 |
|  |  | NS | 0.30 | 0.36 | 0.33 | 0.30 | 0.31 |
|  |  | SLB | 0.39 | 0.48 | 0.45 | 0.42 | 0.43 |
|  |  | ULA | 0.38 | 0.46 | 0.44 | 0.42 | 0.42 |
|  | 50 | DS | 0.42 | 0.37 | 0.29 | 0.26 | 0.26 |
|  |  | EH | 0.48 | 0.49 | 0.42 | 0.40 | 0.40 |
|  |  | EL | 0.39 | 0.40 | 0.30 | 0.28 | 0.29 |
|  |  | NS | 0.38 | 0.41 | 0.36 | 0.34 | 0.34 |
|  |  | SLB | 0.49 | 0.54 | 0.48 | 0.46 | 0.47 |
|  |  | ULA | 0.49 | 0.52 | 0.48 | 0.46 | 0.46 |

IB Maize Populations

The prediction accuracy $r_\Pi$ increased with increasing $N_p$, for all traits and pooling approaches (Table 2). Averaged over traits, the increase was largest for no pooling, where the accuracy increased from an average of 0.35 at $N_p=31$ to 0.48 at $N_p=95$. The accuracies for the partial and complete pooling approaches increased from 0.39 and 0.38, respectively, at $N_p=31$ to 0.48 at $N_p=95$.

At $N_p=31$, partial pooling had the highest $r_\Pi$ for traits EL, KpR, complete pooling for traits DON and KR. For GER both had the same accuracy. The no pooling approach had the lowest $r_\Pi$, except for EL and KpR, where it had the same accuracy as complete pooling. For the highest $N_p$ of 95, the accuracy differences among the pooling approaches decreased. Partial pooling still had the highest accuracy for EL and KpR and the same as complete pooling for DON and GER. While never better than partial pooling, no pooling had higher prediction accuracy than complete pooling for EL and KpR.

TABLE 2

Average within population prediction accuracies in interconnected biparental maize populations. Values shown are average within population prediction accuracies for test individuals, averaged over 100 random estimation-test data splits. Standard errors were <0.01. $N_p$ denotes the average number of individuals per population in the estimation set. The traits were ear length (EL), deoxynivalenol content (DON), *Giberella* ear rot severity (GER) kernel rows (KR) and kernels per row (KpR).

| $N_p$ | Trait | Pooling no | partial | complete |
|---|---|---|---|---|
| 31 | EL | 0.31 | 0.33 | 0.31 |
|  | DON | 0.38 | 0.44 | 0.46 |
|  | GER | 0.38 | 0.43 | 0.43 |
|  | KR | 0.46 | 0.50 | 0.52 |
|  | KpR | 0.21 | 0.23 | 0.21 |
| 62 | EL | 0.40 | 0.41 | 0.39 |
|  | DON | 0.47 | 0.51 | 0.51 |
|  | GER | 0.47 | 0.50 | 0.49 |
|  | KR | 0.53 | 0.56 | 0.58 |
|  | KpR | 0.28 | 0.29 | 0.27 |

TABLE 2-continued

Average within population prediction accuracies
in interconnected biparental maize populations.
Values shown are average within population prediction accuracies
for test individuals, averaged over 100 random estimation-test data splits.
Standard errors were <0.01. $N_p$ denotes the average number of individuals
per population in the estimation set. The traits were ear length (EL),
deoxynivalenol content (DON), *Giberella* ear rot severity (GER)
kernel rows (KR) and kernels per row (KpR).

| $N_p$ | Trait | Pooling no | partial | complete |
|---|---|---|---|---|
| 95 | EL | 0.44 | 0.46 | 0.43 |
|  | DON | 0.51 | 0.53 | 0.53 |
|  | GER | 0.51 | 0.53 | 0.53 |
|  | KR | 0.56 | 0.58 | 0.59 |
|  | KpR | 0.31 | 0.32 | 0.30 |

Simulated Maize Populations

For all pooling approaches, $r_{II}$ increased with decreasing rSD (Table 3). The increase for no pooling, however, was comparatively small and a result of the increasing within family heritability with decreasing rSD. The relative performance of the pooling approaches also depended on rSD. For the highest rSD value considered, no pooling had the highest $r_{II}$, for the intermediate rSD value of 1.0 partial pooling. For the lower rSD values complete and partial pooling achieved similarly high $r_{II}$.

Also $r_\Pi$ for both partial and complete pooling increased strongly with decreasing rSD and the differences to $r_{II}$ decreased (Table 3). Partial and complete pooling achieved almost identical $r_\Pi$.

The mean of the truncated Normal distribution prior $N(m, d^2, 0<a, b=\infty)$ for parameter $\gamma_k$ increased with increasing rSD. Its average values were 0.0111, 0.0153, 0.0190, 0.0269 and 0.0296 for rSD of 0.0, 0.25, 0.5, 1.0 and 2.0, respectively.

TABLE 3

Average prediction accuracies for simulated maize populations.
Values shown are average within population prediction accuracies
for test individuals, averaged over 50 random estimation-test data splits.
Standard errors were <0.015. rSD is the relative standard deviation
of simulated population specific QTL effects.

| rSD | no | $r_{II}$ partial | complete | partial | $r_\Pi$ complete |
|---|---|---|---|---|---|
| 0.0 | 0.54 | 0.89 | 0.89 | 0.89 | 0.89 |
| 0.25 | 0.51 | 0.84 | 0.85 | 0.84 | 0.84 |
| 0.5 | 0.50 | 0.76 | 0.76 | 0.73 | 0.73 |
| 1.0 | 0.48 | 0.57 | 0.53 | 0.48 | 0.49 |
| 2.0 | 0.44 | 0.41 | 0.30 | 0.20 | 0.21 |

Discussion

Comparison of Pooling Approaches

Partial pooling allows estimation of population specific marker effects while still facilitating "borrowing" of information across populations. It is therefore a compromise between no pooling, which models unique characteristics of each population but ignores shared information, and complete pooling, in which the opposite is the case.

When population sizes $N_p$ are sufficiently large, borrowing information from other populations is not required for achieving high prediction accuracy of new individuals from the same population ($r_{II}$). Further enlarging estimation sets by pooling with other populations might then even be detrimental. This explains why no pooling was the most accurate approach when $N_p$ was large (e.g., >=50), particularly in the NAM population, and why it profited most from increases in $N_p$. Therefore, pooling of estimation sets is most promising if $N_p$ is small due to budget or other constraints.

It was observed that pooling was more accurate than no pooling when $N_p$ was small (e.g., <50). The superiority of either pooling approach over no pooling also increased with increasing P, because information from more populations was available, which is not used in no pooling. Thus, pooling is expected to most advantageous when P is relatively high and $N_p$ low. Whether partial or complete pooling is the better approach will then also depend on the similarity of the pooled populations. The greater the similarity, the relatively better complete pooling is expected to perform, because the ability to estimate population specific marker effects becomes less important. In this situation partial pooling might even be of disadvantage, because it requires estimation of many more effects which might lead to problems associated with nonidentifiability. The parents of the IB populations come from the same breeding program, whereas the non-common parents of the NAM populations were chosen to be maximally diverse and comprise temperate, tropical and specialty (sweet and popcorn) maize germplasm. Accommodating for unique characteristics of the populations is therefore more important in NAM than in IB, which might explain why complete pooling was always inferior to partial pooling in the former but often equal or even superior in the latter and also why no pooling never achieved the highest prediction accuracy in IB, even for large $N_p$.

The relative performance of the pooling approaches was very stable across traits in the NAM data set, with the exception of DS. For this trait the no pooling approach was generally superior, even at high P and low $N_p$. Buckler et al. (2009) found evidence for an allelic series at the QTL identified for DS in the NAM population. Thus, while the positions of the QTL are conserved across populations, their effects differ strongly. Possible reasons are presence of multiple alleles or QTL by genetic background interaction. In this situation, pooling of data is not expected to have an advantage over no pooling. This example also shows that decisions about whether to pool data or not have to be made on a by trait basis and should incorporate prior knowledge about genetic architecture, if available.

The dependence of the relative performance of the pooling approaches on the similarity of genetic effects among populations was also reinforced by the results from the simulation study. There it was also observed that the mean of $N(m, d^2, 0<a, b=\infty)$, the prior distribution of $\gamma_k^2$, which quantifies the deviations of specific marker effects $u_{jk}$ from the overall effect $u_k$, increased with increasing simulated differences among population specific QTL effects. This was expected, but demonstrates that the data was informative for the high level hyperparameters. Averaged over P and $N_p$, this mean was largest for DS and ULA in NAM (results not shown). This might reflect the noted differences between population specific QTL effects for DS. Trait ULA, however, did not diverge from the prediction accuracy pattern observed for the remainder of traits and there does not seem to be any strong indication of an allelic series as in DS. There was also no obvious relation between the mean of $N(m, d^2, 0<a, b=\infty)$ and performance of the pooling approaches in IB (results not shown).

Modeling unique characteristics of populations requires that these populations are represented in the estimation set. Prediction of individuals from new populations in Π therefore has to rely on the overall, unspecific marker effects $u_k$, in both partial and complete pooling. It was thus expected that both achieved very similar prediction accuracies $r_\Pi$ for new populations.

These results demonstrate that partial pooling is able to model unique characteristics of populations within the estimation set without compromising on the ability of prediction of individuals from new populations.

This study examplified the use of multilevel models for partial pooling in the context of multiple populations, a scenario of high relevance for plant and animal breeding. However, the concept is readily applicable in a wide array of scenarios. Examples are pooling data across multiple top-cross testers or environments, as is of particular relevance in plant breeding. Extending the models to more than two levels is straightforward, too, for example for pooling multiple populations from multiple heterotic groups or breeding programs.

Composition of Estimation Set

Increasing the number of individuals from a population in the estimation set ($N_p$) always increased prediction accuracy for untested individuals from the same population ($r_{II}$), regardless if the estimation set was further enlarged by individuals from other populations (partial and complete pooling) or not (no pooling).

However, because plant breeding programs have to operate under budget constraints, optimum allocation of resources is of great importance for maximizing the potential of genomic selection. With a fixed budget for phenotyping that is proportional to N, the number of populations P and the number of individuals per population $N_p$ have to be optimized under the constraint that $N=P \cdot N_p$. Such an optimization could be accomplished using basic theory about response to selection and accounting for the different prediction accuracy for populations represented and not represented in the estimation set ($r_{II}$ and $r_{\overline{II}}$, respectively). A key point hereby is that $r_{II}$ will increase with increasing $N_p$ but it will apply to fewer populations because of the decrease in P. This is exacerbated by the decrease in $r_{\overline{II}}$ that we observed was associated with decreasing P. Thus, if the total number of populations is large, as is typically the case in plant breeding programs, having very low P is likely to be undesirable. In the context of plant breeding this study showed that pooling data across populations can at least partly compensate for low $N_p$ if populations are related and there is evidence for the merit of pooling very divergent germplasm too. Using pooled estimation sets therefore has the potential to allow for high P without compromising too much on $r_{II}$. This study showed that partial pooling with multilevel models can further enhance this potential by making optimal use of the information in pooled estimation sets.

What is claimed is:

1. A method for selecting plants in a plant breeding program and for breeding selected plants, said method comprising:
   a. constructing an optimized estimation data set for whole genome prediction and respectively selection by:
      i. selecting and pooling predefined candidate sets of populations, said predefined candidate sets being selected from breeding crosses, and selecting plants within each breeding cross for phenotyping from a comprehensive list of plants targeted for selection wherein genotypic information is available for all candidate plants;
      ii. computing, for a population of breeding crosses and breeding traits under active artificial selection, specific genetic similarity or divergence measures using objective functions of population and trait specific estimated QTL effects;
      iii. constructing optimized estimation datasets in terms of number of populations pooled and respective plants within each population; and
      iv. using partial pooling statistical models as a function of objective genetic similarity or divergence criteria;
   b. phenotyping candidate plants in the optimized estimation data set;
   c. genotyping breeding plants at a plurality of markers;
   d. obtaining genomic estimated breeding values for the genotyped breeding plants using the phenotypes of the candidate plants in the optimized estimation data sets;
   e. making selections within the complete set of genotyped candidate plants for selection plants based on the genomic estimated breeding values generated conditional on optimized estimation sets through partial pooling; and
   f. breeding at least one of the selection plants with at least one other of the selection plants.

2. The method of claim 1, wherein said genotypic information for the candidate plant is obtained via genotyping using SNP markers.

3. The method of claim 1, wherein said breeding plants are homozygous.

4. The method of claim 1, wherein the plant is selected from the group consisting of: maize, soybean, sunflower, sorghum, canola, wheat, alfalfa, cotton, rice, barley, millet, sugar cane and switchgrass.

5. The method of claim 1, wherein the population is a genetically diverse population that includes individuals carrying one or more transgenes.

6. The method of claim 1, wherein the population is a genetically diverse population that includes individuals with DNA edited with Cas9.

7. The method of claim 1, wherein said genotypic information for the candidate is obtained by analyses of gene expression, metabolite concentration, or protein concentration.

* * * * *